(12) United States Patent
Lichtenberger et al.

(10) Patent No.: US 7,838,511 B2
(45) Date of Patent: *Nov. 23, 2010

(54) COMPOSITIONS AND METHODS FOR TREATING, PREVENTING AND/OR AMELIORATING CANCERS, THE ONSET OF CANCERS OR THE SYMPTOMS OF CANCERS

(75) Inventors: Lenard M. Lichtenberger, Houston, TX (US); Elizabeth J. Dial, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 658 days.

This patent is subject to a terminal disclaimer.

(21) Appl. No.: 10/909,751

(22) Filed: Aug. 2, 2004

(65) Prior Publication Data
US 2005/0064025 A1 Mar. 24, 2005

Related U.S. Application Data

(60) Provisional application No. 60/491,676, filed on Jul. 31, 2003.

(51) Int. Cl.
*A61K 31/685* (2006.01)
(52) U.S. Cl. ..................................... 514/78
(58) Field of Classification Search ........... 514/78
See application file for complete search history.

(56) References Cited

U.S. PATENT DOCUMENTS

| 4,309,421 A | | 1/1982 | Ghyczy et al. |
| 4,421,747 A | * | 12/1983 | Ghyczy et al. ............... 514/78 |
| 5,466,694 A | | 11/1995 | Terranova et al. |
| 5,505,960 A | | 4/1996 | Lucchetti et al. |
| 5,955,451 A | * | 9/1999 | Lichtenberger et al. ....... 514/78 |
| 6,120,797 A | | 9/2000 | Meers et al. |
| 6,231,888 B1 | * | 5/2001 | Lerner et al. ............... 424/463 |

FOREIGN PATENT DOCUMENTS

| EP | 0 313 347 A2 | 10/1988 |
| EP | 1 214 940 A1 | 1/1996 |
| WO | WO 02/085414 A2 | 10/2002 |

OTHER PUBLICATIONS

Dang et al., "Adjuvant taxanes in the treatment of breast cancer: no long at the tip of the iceberg.", Clin Breast Cancer, Apr. 2006, 7(1): 51-8 (Abstract only).*
Cecil Textbook of Medicine (20th Edition), Bennett et al., 1997, P1004-1010.*
Sausville et al. Contributions of human tumor xenografts to anticancer drug development. Cancer Research, 2006, vol. 66, pp. 3351-3354.*
Johnson et al. Relationships between drug activity in NCI preclinical in vitro and in vivo models and early clinical trials. British J. of Cancer, 2001, 84(10):1424-1431.*
Jenkins et al. Palliative Medicine, 1999, vol. 13, pp. 183-196.*
Lebeau et al. Cancer, 1993, vol. 71, pp. 1741-1745 (Abstract attached).*
Calaluce et al. Cancer Epidemiology, Biomarkers & Prevention, Dec. 2000, vol. 9, pp. 1287-1292.*
Knapp et al. Cancer Chemother. Pharmacol., 1992, vol. 29, pp. 214-218.*
Andrews et al. Cancer Chemother. Pharmacol., 2002, vol. 50, pp. 277-284.*
Alino SF, Iruarrizaga A, Alfaro J, Almena A, Lejarreta M, Unda FJ. Antimetastatic effects of liposome entrapped indomethacin. Life Sci. 1991;48(2):149-54.
International Search Report and the Written Opinion of the International Searching Authority. U.S. Patent and Trademark Office. Jan. 10, 2005.
Supplementary European Search Report Under Article 157(2)(a) EPC . European Patent Office. Sep. 22, 2006.
Israeli Patent Office, Official Action, Serial No. 173352, Mar. 4, 2010.
European Patent Office, Response to Official Action, Serial No. 04779761.8, Apr. 22, 2010.
Chinese Patent Office, Request for Reexamination and claims, Serial No. 2004800264983, Apr. 23, 2010.

* cited by examiner

*Primary Examiner*—James D Anderson
(74) *Attorney, Agent, or Firm*—Jackson Walker L.L.P.

(57) ABSTRACT

Compositions and methods are disclosed for treating, preventing and/or ameliorating the symptoms of cancers such as breast cancer, colon cancer, ovarian cancer, lung cancer, leukemia, skin cancer, prostate cancer, throat cancer, esophageal cancer etc., where the composition includes an associated complex of a nonsteroidal, anti-inflammatory drug (NSAID) and a phospholipid and the method includes administering before or after cancer identification an anti-cancer amount of the compositions.

2 Claims, 5 Drawing Sheets

COMPOSITIONS AND METHODS FOR TREATING, PREVENTING AND/OR AMELIORATING CANCERS, THE ONSET OF CANCERS OR THE SYMPTOMS OF CANCERS

RELATED APPLICATIONS

This application claims provisional priority to U.S. Provisional Application Ser. No. 60/491,676, filed Jul. 31, 2003.

BACKGROUND OF THE INVENTION

1. Field of the Invention

The present invention relates to compositions and methods for treating, preventing and/or ameliorating cancers, the onset of cancers or the symptoms associated with cancers such as breast cancer, colon cancer, skin cancer, lung cancer, throat cancer, esophageal cancer, gastric cancer, pancreatic cancer, prostate cancer, bladder cancer, etc.

More particularly, the present invention relates to compositions and methods for treating, preventing and/or ameliorating cancers, the onset of cancers or the symptoms associated with cancers such as breast cancer, colon cancer, skin cancer, lung cancer, throat cancer, esophageal cancer, gastric cancer, pancreatic cancer, prostate cancer, bladder cancer, etc., where the compositions comprises a nonsteroidal anti-inflammatory drug (an NSAID) and a phospholipid where the phospholipid enhances the anti-cancer efficacy of the NSAID and the methods include administering the composition to a human or animal before or after cancer identification and where the method of administration can be oral, topical, intra-venous, intra-arterial or directly into a tissue site.

2. Description of the Related Art

Cancer is the disease responsible for the majority of deaths in both the U.S. and worldwide. Although the advent of new chemotherapeutic regimens has increased patient survival once cancer is diagnosed, it has not reduced the overall incidence or severity of the disease.

Nonsteroidal anti-inflammatory drugs (NSAIDs) have been suggested for chemoprevention of breast; colon, and other cancers based on epidemiological studies showing an inverse association between use of NSAIDs and cancer risk (1, 2). There is supporting preclinical and clinical data to suggest that NSAIDs may offer a chemopreventive strategy that is effective and inexpensive. The main limiting side effect to the use of NSAIDs is their tendency to cause gastrointestinal (GI) bleeding and lesions in susceptible patients.

NSAIDs are currently subdivided into two classes: 1) the conventional drugs like aspirin, ibuprofen (Advil or Motrin), or naproxen (Aleve), which inhibit both the constitutive cyclooxygenase-1 (COX-1) and inducible cyclooxygenase-2 (COX-2) enzyme isoforms, respectively, that serve as the rate-limiting enzymes in the conversion of arachidonic acid to prostaglandins, and 2) the recently developed and commercialized selective COX-2 inhibitors like celecoxib (Celebrex) and rofecoxib (Vioxx) (3).

The mechanism by which COX inhibition may affect cancer is under investigation and probably involves multiple factors. High expression of COX-2 results in elevated prostaglandin formation, molecules which stimulate cell proliferation (4-5). COX-2 and prostaglandins are also implicated in the induction of angiogenesis by production of factors such as vascular endothelial growth factor (6). Therefore, NSAID inhibition of these proliferative properties of prostaglandins would clearly promote anti-tumor activity. In addition, NSAIDs have recently been shown to possess COX-independent anti-cancer activity, through the induction of NSAID activated gene (NAG-1), a proapoptotic and antitumorigenic factor (7-10). NSAIDs also may affect cancer growth through inhibition of NFκB activation (11-12), by inducing the pro-apoptotic BAX gene and inhibiting the anti-apoptotic Bcl-XT protein (13), and by inducing apoptosis through activation of protein kinase G and c-Jun kinase (14).

Although the administration of conventional or COX-2 selective NSAIDs in chemoprevention of cancer has great promise, the chronic consumption of these drugs is not without risk and/or problems. The major concern with the chronic usage of these drugs is that 30-40% of consumers have a GI intolerance to NSAIDs, and suffer from a spectrum of symptoms, ranging from dyspepsia to peptic ulcer disease, which may be associated with life-threatening episodes of hemorrhage (15). One clinical study demonstrated that 30% of chronic NSAID users had at least one gastroduodenal ulcer at endoscopy (15-16). Furthermore, a retrospective study restricted to rheumatoid arthritis patients in the U.S. concluded that GI complications due to NSAID usage is responsible for 400,000 hospitalizations and 16,000 deaths annually in this patient population alone (15). It also should be noted that NSAIDs do not have to be administered at high antiarthritic doses to induce serious GI side-effects, with evidence suggesting that the population with the greatest number of NSAID-associated GI complications requiring hospitalizations, constitute the millions of people taking low-dose aspirin for prevention of cardiovascular disease and/or cancer (17-18).

Thus, there is a need in the art for new prophylactic compositions for the prevention of the onset of cancerous growth, for the treatment of identified cancerous growths and/or for the amelioration of the symptoms associated with cancerous growth, tumor or not.

SUMMARY OF THE INVENTION

The present invention provides a compositions for treating, preventing or ameliorating the symptoms associated with cancer or cancerous growths, where the composition includes a phospholipid and an anti-inflammatory pharmaceutical including a nonsteroidal, anti-inflammatory pharmaceutical (NSAID), a COX-2 inhibitor and mixtures or combinations thereof, preferably an associated complex of a phospholipid and an anti-inflammatory pharmaceutical. The compositions of this invention can include one or more phospholipid and an anti-inflammatory pharmaceutical compositions varying in both phospholipid and anti-inflammatory pharmaceutical. Such compositions can be mixtures of separately prepared phospholipid and an anti-inflammatory pharmaceutical compositions or composition including one or more phospholipid and/or one or more phospholipid and an anti-inflammatory pharmaceutical.

The present invention also provides a filter sterilized compositions for treating, preventing or ameliorating the symptoms of cancer or cancerous growth, where the composition includes an associated complex of a phospholipid and a nonsteroidal, anti-inflammatory pharmaceutical or an NSAID.

The present invention provides methods for treating, preventing and/or ameliorating the symptoms of cancer or cancerous growths including the steps of administering, orally, topically, intravenously, intra-arterially, directly into a human or animal tissue site or a combination of such administration protocol a composition including an associated complex of a phospholipid and a nonsteroidal, anti-inflammatory pharmaceutical or a filter sterilized composition including an associated complex of a phospholipid and a nonsteroidal, anti-inflammatory pharmaceutical or an NSAID.

The present invention provides methods for making sterile preparations including the steps of contacting an aqueous phospholipid composition and an anti-inflammatory pharmaceutical under agitating conditions at a given pH range to form an agitated phospholipid/anti-inflammatory pharmaceutical preparation and passing the agitated preparation through a membrane filter having a pore size sufficiently small to produce a filter sterilized phospholipid/anti-inflammatory pharmaceutical preparation. For further details on the preparation of sterile filterable phospholipid/anti-inflammatory pharmaceutic compositions the reader is referred to co-pending U.S. patent application Ser. No. 10/909,748 filed using express mail label EV 405 879 065 US contemporaneously with this filing on 2 Aug. 2004, incorporated herein by reference.

The present invention provides a hand or body soap including an effective amount of a composition including a phospholipid and a nonsteroidal, anti-inflammatory pharmaceutical or an NSAID, preferably an associated complex of a phospholipid and a nonsteroidal, anti-inflammatory pharmaceutical, where in the effective amount is sufficient to prevent the onset of skin cancer, treat skin cancer or ameliorate the symptoms of skin cancer.

The present invention provides a sun block including an effective amount of a composition including a phospholipid and a nonsteroidal, anti-inflammatory pharmaceutical or an NSAID, preferably an associated complex of a phospholipid and a nonsteroidal, anti-inflammatory pharmaceutical, where in the effective amount is sufficient to prevent the onset of skin cancer, treat skin cancer or ameliorate the symptoms of skin cancer.

The present invention provides a body cream including an effective amount of a composition including a phospholipid and a nonsteroidal, anti-inflammatory pharmaceutical or an NSAID, preferably an associated complex of a phospholipid and a nonsteroidal, anti-inflammatory pharmaceutical, where in the effective amount is sufficient to prevent the onset of skin cancer, treat skin cancer or ameliorate the symptoms of skin cancer.

The present invention provides a face cream including an effective amount of a composition including a phospholipid and a nonsteroidal, anti-inflammatory pharmaceutical or an NSAID, preferably an associated complex of a phospholipid and a nonsteroidal, anti-inflammatory pharmaceutical, where in the effective amount is sufficient to prevent the onset of skin cancer, treat skin cancer or ameliorate the symptoms of skin cancer.

DEFINITIONS

Unless otherwise stated, the following terms shall have the following meanings:

The term "fluid" means a liquid and any mixture of a liquid and a solid that has fluid attributes, e.g., flowable or having appreciable fluidity a standard temperature and pressure, including, without limitation, a dispersion of a solid(s) in a liquid, an emulsion, a slurry, a micro-emulsion, colloidal suspension, a suspension, or the like.

The term "molecular association or associated complex" means a combination of two or more molecular species associated via any known stabilizing atomic or molecular level interaction or any combination thereof, where the interactions include, without limitation, bonding interactions such as covalent bonding, ionic bonding, hydrogen bonding, coordinate bonding, or any other molecular bonding interaction, electrostatic interactions, a polar or hydrophobic interactions, or any other classical or quantum mechanical stabilizing atomic or molecular interaction.

The term "animal" is defined as any species in the animal kingdom including mammals.

The term "mammal" is defined as any class of warm-blooded higher vertebrates that includes humans.

The term "phospholipid" refers any lipid or fatty acid having a covalently attached a phosphate group in the molecular structure.

The term "zwitterionic phospholipid" means a phospholipid having a proton acceptor in the molecular structure so that the phosphate group can bear a negative charge and the proton acceptor can be a positive charge due to an intramolecular acid-base reaction.

The term "heterocyclyl" means a saturated or unsaturated 5 to 7-membered heterocyclic group with one or two rings and 1 to 3 heteroatoms, independently chosen from N, O or S.

The term "aryl" denotes a substituted or unsubstituted phenyl, furyl, thienyl or pyridyl group, or a fused ring system of any of these groups, such as naphtyl.

The term "substituted aryl" denotes an aryl group as defined above which is substituted by one or more alkyl, alkoxy, halogen, amino, thiol, nitro, hydroxy, acyl, aryl or cyano groups.

The term "colloidal metal" denotes any metal or metal-containing compound that can be formed into a colloidal suspension or dispersion.

The term "metal complex" denotes complexes of any metal classified as such in the Periodic Chart of Elements and preferably, complexes of non-alkali metals.

The term "polyvalent metal complex" denotes any complex of a metal, where the metal can have, carry or bear a positive charge greater than 1 and generally from 2 to 6.

The term "zwitterion" denotes a molecule having both a positive charged group and a negatively charged group.

The term "zwitterionic form" denotes a molecule that has a positive charged group and a negatively charged group. Generally, the reaction conditions are adjusted so that intramolecular hydrogen ion transfer can occur.

The term "pharmaceutically effective amount" denotes an amount of NSAID required to cause a measurable reduction in an NSAID affected symptoms such as pain reduction, fever reduction, inflammation reduction, or the like.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
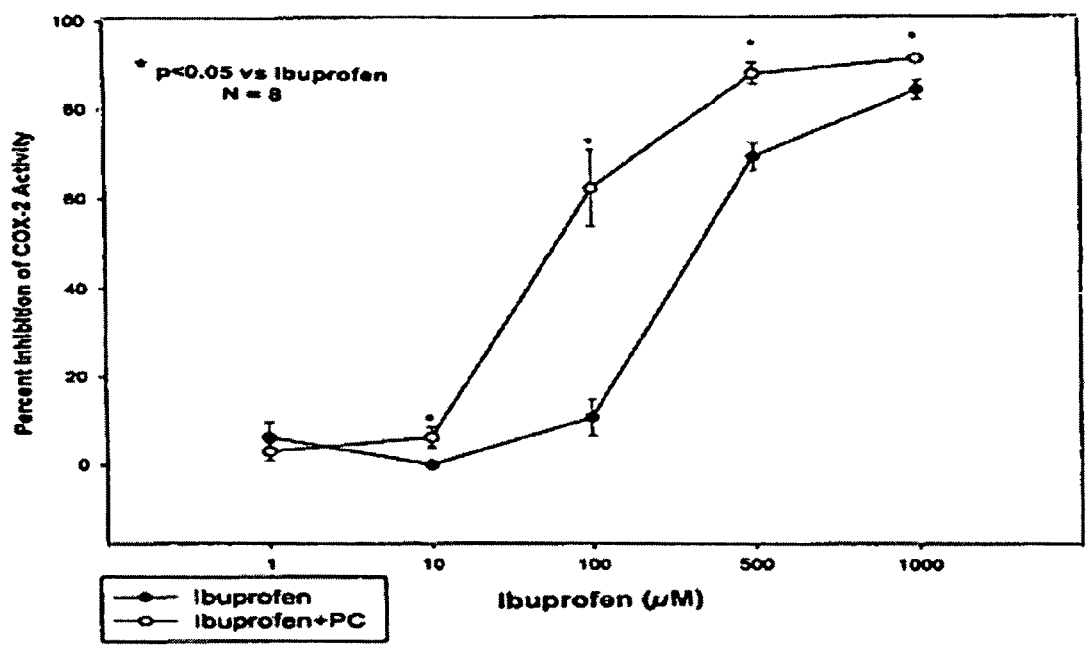
FIG. 1 depicts comparison of the potency of ibuprofen to Phospholipid-ibuprofen to inhibit COX-2 activity of TPA-activated HUVECs.

The inventors have found that a composition including a phospholipid and an anti-inflammatory pharmaceutical improves the anti-cancer effects of the anti-inflammatory pharmaceutical relative to the anti-inflammatory pharmaceuticals administered in the absence of the phospholipid. These results provide a composition and method for treating, preventing or ameliorating symptoms associated with cancers or cancerous growths by contacting the cells of the cancer or cancerous growth with the compositions of this invention alone or in conjunction with other anti-cancer treatments. Moreover, the present compositions can be administered orally, topically, and/or internally as a therapeutic and/or prophylactic preventative. Furthermore, the present compositions can be added to hand soaps, sun blocks, or other cosmetics as a prophylactic preventative to skin damage and the ultimate onset of skin cancers.

The prophylactic use of nonsteroidal, anti-inflammatory drugs (NSAIDs) to prevent cancer has gained acceptance for patients at risk for colorectal cancers. The possible use of NSAIDs in prevention of breast cancer is under consideration, and is supported by a number of in vitro and in vivo studies. The major limiting side effect to the chronic use of NSAIDs is their propensity to induce bleeding and ulceration of the gastrointestinal tract in susceptible individuals. The addition of a phospholipid such as phosphatidylcholine (PC) to an NSAID results in little or no GI injury after acute or chronic dosing in animals and humans. Additionally, the combination of a phospholipid such as PC and an NSAID, so-called PC-NSAIDs, have shown a greater ability to relieve pain, fever, and inflammation than unmodified NSAIDs.

The present invention broadly relates to a method for preventing, treating or ameliorating the symptoms of cancer or cancerous growths including the steps of administering a composition comprising an associated complex of a phospholipid and an NSAID to an animal including a human according to an administration protocol, where the administration protocol including one or more administrations including oral administration, topical administration, intravenous administration, intra-arterial administration, or directly administration into a tissue site.

Although the compositions of this invention can be used separately, they can also be used in conjunction with other chemotherapies, immunotherapy and radiation therapies. Thus, the compositions of this invention can be administered before, after or during radiation therapy. The compositions of this invention can also be administered before, during or after administration with other chemo-therapeutic agents.

Suitable radiation therapy include, without limitation, high-energy radiation from x-rays, gamma rays, neutrons, and other sources to kill cancer cells and shrink tumors. Radiation may come from a machine outside the body (external-beam radiation therapy), or it may come from radioactive material placed in the body near cancer cells (internal radiation therapy, implant radiation, or brachytherapy). Systemic radiation therapy uses a radioactive substance, such as a radiolabeled monoclonal antibody, that circulates throughout the body. Also called radiotherapy.

Suitable immunotherapies include, without limitation, cancer vaccines (active specific immunotherapies), monoclonal antibody therapy (passive immunotherapies) and non-specific immunotherapies and adjuvants.

Suitable chemotherapies include, without limitation, alkylating agents, agents that interfere with the growth of cancer cells by blocking the replication of DNA; antimetabolites, that block the enzymes needed by cancer cells to live and grow; antitumor antibiotics, that interfere with DNA, blocking certain enzymes and cell division and changing cell membranes, and mitotic inhibitors, that inhibit cell division or hinder certain enzymes necessary in the cell reproduction process.

Suitable phospholipids for use in this invention include, without limitation, a phospholipid of general formula:

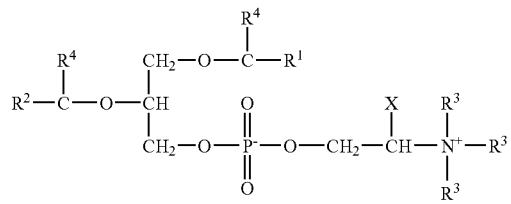

where R' is H, OH or Cl and R is: (a) an alkyl group having 1 to 6 carbon atoms, optionally substituted with amino, alkylamino. dialkylamino or heterocyclyl, where the alkyl groups in alkylamino and dialkylamino substituents have 1 to 5 carbon atoms and are the same or different in the case of the dialkylamino substituted alkyl groups; (b) a halogen; (c) an arylthio, preferably chlorosubstituted; (d) a cycloalkylamino having 5 to 7 carbon atoms; or (e) a saturated five or six membered nitrogen containing heterocyclyl having 1 or 2 heteroatoms; and $R_1$ and $R_2$ are saturated or unsaturated substitutions ranging from 8 to 32 carbon atoms; $R_3$ is H or $CH_3$, and X is H or COOH; and $R_4$ is =O or $H_2$. Mixtures and combinations of the zwitterionic phospholipids of the general formula and mixtures and combinations of NSAIDs can be used as well.

Exemplary examples of zwitterionic phospholipid of the above formula include, without limitation, phosphatidylcholines such as phosphatidyl choline (PC), dipalmitoylphosphatidylcholine (DPPC), other disaturated phosphatidylcholines, phosphatidylethanolamines, phosphatidylinositol, phosphatidylserines sphingomyelin or other ceramides, or various other zwitterionic phospholipids, phospholipid containing oils such as lecithin oils derived from soy beans, dimyristoylphosphatidylcholine, distearoylphosphatidylcholine, dilinoleoylphosphatidylcholine (DLL-PC), dipalmitoylphosphatidylcholine (DPPC), soy phophatidylchloine (Soy-PC or $PC_S$) and egg phosphatidycholine (Egg-PC or $PC_E$). In DPPC, a saturated phospholipid, the saturated aliphatic substitution $R_1$ and $R_2$ are $CH_3$—$(CH_2)_{14}$, $R_3$ is $CH_3$ and X is H. In DLL-PC, an unsaturated phospholipid, $R_1$ and $R_2$ are $CH_3$—$(CH_2)_{14}$, CH=CH—$CH_2$—CH=CH—$(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid). In Soy-PC, which in addition to the saturated phospholipids (palmitic acid and stearic acid) is a mixture of unsaturated phospholipids, [oleic acid, linoleic acid and linolenic acid]. The preferred zwitterionic phospholipid include, without limitation, dipalmitoyl phosphatidylcholine, phosphatidyl choline, or a mixture thereof.

Suitable NSAIDS include, without limitation, Propionic acid drugs such as Fenoprofen calcium (Nalfon®), Flurbiprofen (Ansaid®), Suprofen. Benoxaprofen, Ibuprofen (prescription Motrin®), Ibuprofen (200 mg. over the counter Nuprin, Motrin 1B®), Ketoprofen (Orduis, Oruvall®), Naproxen (Naprosyn®), Naproxen sodium (Aleve, Anaprox, Aflaxen®), Oxaprozin (Daypro®), or the like; Acetic acid drug such as Diclofenac sodium (Voltaren®), Diclofenac potassium (Cataflam®), Etodolac (Lodine®), Indomethacin (Indocin®), Ketorolac tromethamine (Acular, Toradol® intramuscular), Ketorolac (oral Toradol®), or the like; Ketone drugs such as Nabumetone (Relafen®), Sulindac (Clinoril®), Tolmetin sodium (Tolectin®), or the like; Fenamate drugs such as Meclofenamate sodium (Meclomen®), Mefenamic acid (Ponstel®), or the like; Oxicam drugs such as Piroxicam (Dolibid®), or the like; Salicylic acid drugs such as Diflunisal (Feldene®), Aspirin, or the like; Pyrazolin acid drugs such as Oxyphenbutazone (Tandearil®), Phenylbutazone (Butazolidin®), or the like; acetaminophen (Tylenol®), or the like or mixtures or combinations thereof.

Suitable COX-2 inhibitors for using in this invention include, without limitation, celecoxib, meloxicam, diclofenac, meloxicam, piroxicam, or newly approved COX-2 inhibitors or mixtures or combinations thereof.

Generally, the weight ratio of NSAID to zwitterionic phospholipid is between about 1:0.01 and about 1:100, with ratios between about 1:0.02 and 1:50 being preferred and ratios between about 1:0.1 and 1:10 being particularly preferred and ratios between about 1:1 and about 1:5 being especially preferred. The effective amount of the NSAID for use in the composition of this invention ranges from about 1 mg per dose to about 1000 mg per dose depending on the NSAID and the phospholipid used in the composition, with doses between about 50 mg per dose to about 1000 mg per does being preferred, doses of 83 mg per dose (for ASA), or about 100 mg per dose, of about 200 mg per dose, of about 400 mg per dose, of about 500 mg per dose, of about 600 mg per dose, of about 800 mg per dose and of about 1000 mg per dose being particularly preferred. A sufficient amount of phospholipid is generally an amount of phospholipid between about 0.1 mg per dose to about 5000 mg per dose, with amounts between about 1 mg per dose to 2500 mg per dose being preferred and amount between 2 mg per dose to about 250 mg per dose being particularly preferred and amounts between about 2 mg per dose and about 100 mg per does being especially preferred.

The associated complexes of this invention can be prepared according to the methods set forth in the following U.S. Pat. Nos. 5,955,451; 5,763,422; 5,260,287; 5,260,284; 5,134,129; 5,043,329; 5,032,464; 4,950,658 and 4,918,063, and co-pending U.S. patent application Ser. No. 10/433,454; incorporated herein by reference.

Generally, the compositions of this invention are formulated to be taken according to a given administration protocol depending on the nature of the cancer and the recommended treatment protocol alone or in conjunction with other anti-cancer treatment protocol.

The compositions of the present invention can be in any desirable form, including, without limitation, a solid such as a powder, granules, tablets, pills, capsules, gel coated tablets or pills, or the like, a semi-solid such as a paste or the like, a suspension, a dispersion, an emulsion, or a solution. Dispersions or suspensions means that a solid form of the compositions of the present invention are mixed with a suitable solvent in which the composition has no or relatively low solubility, i.e., a solubility less than about 10 wt. %, preferably less than about 5 wt. % and particularly less than about 1 wt. %. An emulsion means that an oil or aqueous form of the compositions of this invention are emulsified in an aqueous solution or oil, respectively, i.e. oil-in-water emulsions or water-in-oil emulsions. In addition, the emulsion can be a standard emulsion or a micro-emulsion where the emulsifying is added by passing the mixture through a nozzle or in other methods that generate micro-emulsions. A solution means that the compositions of this invention are in a suitable solvent in which the composition is soluble or highly soluble. This invention also includes formulations in which NSAID is suspended and/or dissolved in PC enriched oil such as soy bean oil.

Methods for Making NSAID/Phospholipid Compositions

One preferred class of compositions of this invention are compositions that include a NSAID and a phospholipid generally prepared by contacting a NSAID and a phospholipid under conditions to promote molecular association of the NSAID and phospholipid in their zwitterionic forms. Such conditions typically will include use of a solvent and/or buffer, use of mixing procedures that promote molecular interactions and associations, and controlled temperature, pressure and time to permit a desired degree of intermolecular interaction and association. Because these two classes of chemicals can exist as zwitterions in polar solvents, intermolecular interactions and associations between these two classes of compounds can be facilitated either by using a solvent or by using a buffer of low ionic strength, so called hypotonic buffers. In some cases, the NSAID will be added to the PC or deoiled lecithin in the organic solvent prior to its removal by evaporation.

Generally, the hypotonic buffers include water with buffering compounds added to from a buffer having a molarity of between about 1 millimolar to about 100 millimolar. These low ionic strength buffers promote intermolecular interactions and/or associations between the zwitterionic forms of the NSAID and phospholipid by reducing interactions between the NSAID and the buffer and the phospholipid and the buffer.

The contacting is also performed in the presence of mixing, and preferably aggressive or vigorous mixing. Such mixing procedures include sonication or other molecular level mixing procedures, vortex mixing or other high shear mixing procedures, or the like. The time and temperature of mixing should be designed to maximize intermolecular interactions between the zwitterionic forms of the NSAID and the phospholipid without causing thermal or shear damage to the molecules themselves. Generally, the mixing time will range from about 5 minutes to several hours, with times ranging between 10 minutes and 1 hour being preferred. Generally, the mixing temperature will range from ambient to a temperature at least 10% below the lowest breakdown temperature for the NSAID or phospholipid being mixed or at least 10% below the boiling point of the lowest boiling solvent or 10% below a temperature at which the buffer begins to decompose or loss its buffering capacity. Preferably, the temperature will be between ambient temperature to about 70° C.

The pH of the buffer can also play a role in the promotion of intermolecular interactions and/or associates between the NSAID and phospholipid. Generally, for most NSAIDs and COX-2 inhibitors, the pH is in a range between about 3 and about 10, and preferably between about 4 and 8. Preferably, the pH is adjusted at or near (within 2 pH units) of the NSAID's or COX-2 inhibitor's $PK_a$ value.

In preparing the formulations of this invention, the NSAIDs can be mixed with purified naturally derived or synthetic phospholipid or can be mixed with various grades of lecithin (extracted from soy lecithin available from American Lecithin Co) or other natural oils high in phospholipids. Especially useful lecithins have phospholipid concentrations ranging from about 15 to about 93% PC by weight. Moreover, the formulations can use either de-oiled and oiled-based lecithin preparations.

Regardless of the form of the phospholipid, generally the ratio of NSAID to phospholipid ranges from about 1.0:0.01 to about 1:100, preferably, from about 1.0:0.5 to about 1:25, and particularly from about 1.0:1.0 to about 1.0:10.0.

In formulations using deoiled lecithins, the deoiled lecithins are initially dissolved in an organic solvent such as ethanol, where the organic solvent is removed by evaporation under nitrogen or under a vacuum or lyophilized and then resuspended in a NSAID containing solution, followed by mixing such as vortexing and/or sonication mixing under moderate heating if need (above room temperature to about 75° C.). In formulations using lecithins, the oiled-based lecithin is simply combined with a NSAID compounds and mixed by vortexing and/or sonication, if needed.

Another preferred method for making the compositions of this invention is to dissolve the NSAIDs in hypotonic aqueous solution or buffer having a molarity between about 1 and about 100 millimolar (mM). Suitable solutions and/or buffers include, without limitation, NaCl solutions, Tris buffers, bicarbonate buffers, HEPES buffers, MOPS buffers or the like.

Sonication or mixing temperatures are preferably preformed at a temperature above the transition temperature, $T_m$, of the phospholipid, i.e., the temperature at which the phospholipid undergoes a phase transitions from a liquid crystalline state to a gel state as is well-known in the art). In the case of PC, the mixing can be performed at room temperature, while for DPPC, the mixing is performed above 42° C.

Another preferred process for making the compositions of this invention includes to dissolving the phospholipid and the NSAID in a polar solvent. Suitable solvent include, without limitation, chlorocarbons such as chloroform, or the like, lower alcohols such as methanol, ethanol, isopropanol or the like, or any other solvent in which the phospholipid and the NSAID have some solubility, with the added condition that the solvent be readily removable by either evaporation or the like.

When a metal complex is used, the complex can be added directly into the phospholipid and the NSAID solution. Alternatively and preferably, the complex and the NSAID can be prepared in a hypotonic buffer that is added a preformed phospholipid film as described herein.

Cosmetic Compositions Including NSAID/Phospholipid Compositions

A skin care composition comprising a cosmetically acceptable composition including from about 0.001 to about 25 wt. % of an associated complex of a phospholid and an NSAID, where the wt. % is relative to a total weight of composition ingredients, preferably, from about 0.1 to about 25 wt. % of an associated complex of a phospholid and an NSAID, particularly, from about 1 to about 25 wt. % of an associated complex of a phospholid and an NSAID, more particularly, from about 2 to about 20 wt. %, and even more particularly, from about 2 to about 10 wt. % of an associated complex of a phospholid and an NSAID.

The cosmetically acceptable composition further comprises an anionic, cationic, non-ionic surfactan or mixtures or combinations thereof. The cosmetically acceptable composition further comprises one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, Catty alcohols, ethoxylated fatty alcohols and di-tail phospholipids.

The cosmetically acceptable composition is selected from the group consisting of shampoos, aftershaves, sunscreens, hand lotions, skin creams, liquid soaps, bar soaps, bath oil bars, shaving creams, dishwashing liquids, conditioners, shower gels, bubble baths, or the like.

The cosmetically acceptable composition is selected from the group consisting of shampoos, aftershaves, sunscreens, hand lotions, skin creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

The cosmetically acceptable composition further comprises one or more surfactancts selected from the group consisting of anioinic, cationic, nonionic or mixtures or combinations thereof, one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about C10 to C22, long chain fatty amines from about C10 to C22, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomainans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994) which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., SO3, H2 S04, oleum, obtained according to known sulfonation methods, including bleaching and hydrolysis. Preferred are alkali metal and ammonium sulfated C12-38 n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowdimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowdimonium chloride, myristalkonium chloride, PEG-2 Oleamonium chloride, PEG-5 Stearmonium chloride, PEG-15 cocoyl quatemium 4, PEG-2 stearalkonium 4, lauryltrimonium chloride; Quaternium-16; Quaternium-18, lauralkonium chloride, olealkrmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Coming®, Midland, Mich., USA. Additional alkyl and phenyl silicones may be employed to enhance moisturizing properties. Resins such as dimethicone (and) trimethylsoiloxysilicate, known as Dow Coming® 593 or Cyclomethicone (and) Trimethylsiloxysilicate, known as Dow Corning®749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof.

Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the tradename Dow Coming®200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the tradenames Dow Coming®244 fluid, Dow Coming®245 fluid, Dow Coming®246, Dow Coming®344 fluid and Dow Coming®345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Coming®3225C and 5225C Formulation Aids, available from Dow Coming, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning®5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent (wt. %), more preferably 1 to 15 weight percent.

Amine functional silicones and emulsions may be utilized in the present invention. Preferred examples include Dow Coming®8220, Dow Coming®939, Dow Coming®949, Dow Coming®2-8194, all available from Dow Coming, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17.sup.th Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10-30 Alkyl Acrylate Crosspolymer, such as the Carbopol® and Pemulen® series, both available from B. F. Goodrich, Akron, Ohio, USA; anionic acrylate polymers such as Salcare®.AST and cationic acrylate polymers such as Salcare®SC96, available from Ciba Specialties, High Point, N.C., USA; Acrylamidopropylttrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn®28, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD®, ONDEO Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

The cosmetic formulations are prepared by general well known mixing and blending technologies. The PC-NSAID compositions of this invention can be premade or made in situ during the manufacturing process provided that the PC and NSAID can form an associate complex.

Other soap and cosmetic formations and composition to which an associated complex of a phospholipid and an NSAID can be added are disclosed in U.S. Pat. Nos. 6,767, 878; 6,696,397; 6,696,067; 6,613,866; 6,613,755; 6,610,315; 6,586,590; 6,583,181; 6,555,708; 6,518,229; 6,517,846; 6,440,908; 6,429,180; 6,383,997; 6,312,703; 6,271,187; 6,187,728; 6,147,039; 6,121,214; 6,087,400; 6,060,808; 6,025,312; 5,994,383; 5,994,286; 5,962,399; 5,942,478; 5,854,197; 5,490,955; 5,419,908; 5,395,541; 5,338,541; 5,136,093; 5,075,042; 5,041,236; 4,959,171; 4,617,148; and 4,548,810, incorporated herein by reference.

Experimental Section

Referring first to FIG. 1, a comparison of the potency of ibuprofen to Phospholipid associated ibuprofen (PC-IBU) to inhibit COX-2 activity of TPA-activated HUVECs is shown. The data demonstrated that the PC imparts enhanced effacy to ibuprofen in inhibiting COX-2 activity of 12-O-tetradecanoylphorbol-13-acetate (TPA)-activated human umbilical vein endothelial cells (HUVECs) as compared to ibuprofen alone.

Figure 2:
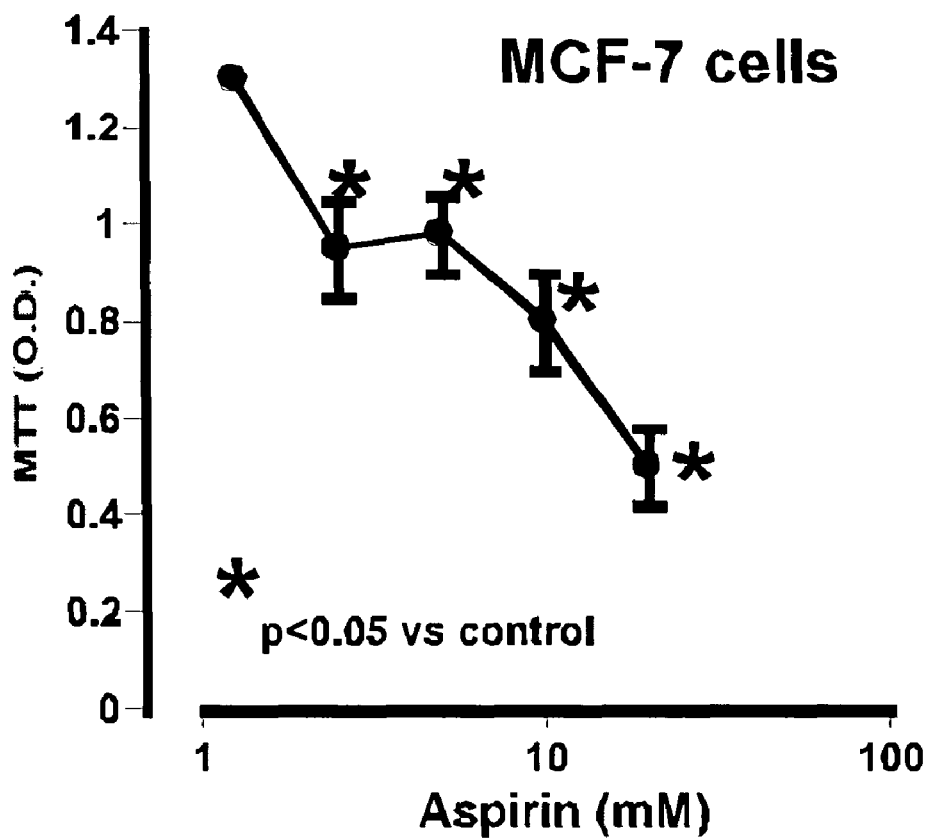
FIG. 2 depicts dose-response of ASA on growth of MCF-7 cells [Control value (0 mM ASA) is the same as 1.25 mM ASA]

Using MCF-7 breast cancer cells grown in culture, a dose-response to aspirin (1.25 to 20 mM) was performed initially. After 48 hours of exposure to the various aspirin (acetyl salicylic acid, ASA) concentrations, mitochondrial 3-(4,5-dimethylthiazol-2-yl)-2,5-diphenyltetrazolium bromide (MTT) assays were performed. The MTT assay produces a measure of cell number and is used to monitor growth or inhibition of growth of the MCF-F breast cancer cells, i.e., measure the relative growth inhibitor activity of the compositions. As shown in FIG. 2, where ASA concentration is plotted on a log scale of milli molarity (mM), ASA was found, under these conditions, to have an inhibitor activity or effect on the growth of the cells at concentrations of 2.5 mM and higher.

Figure 3:
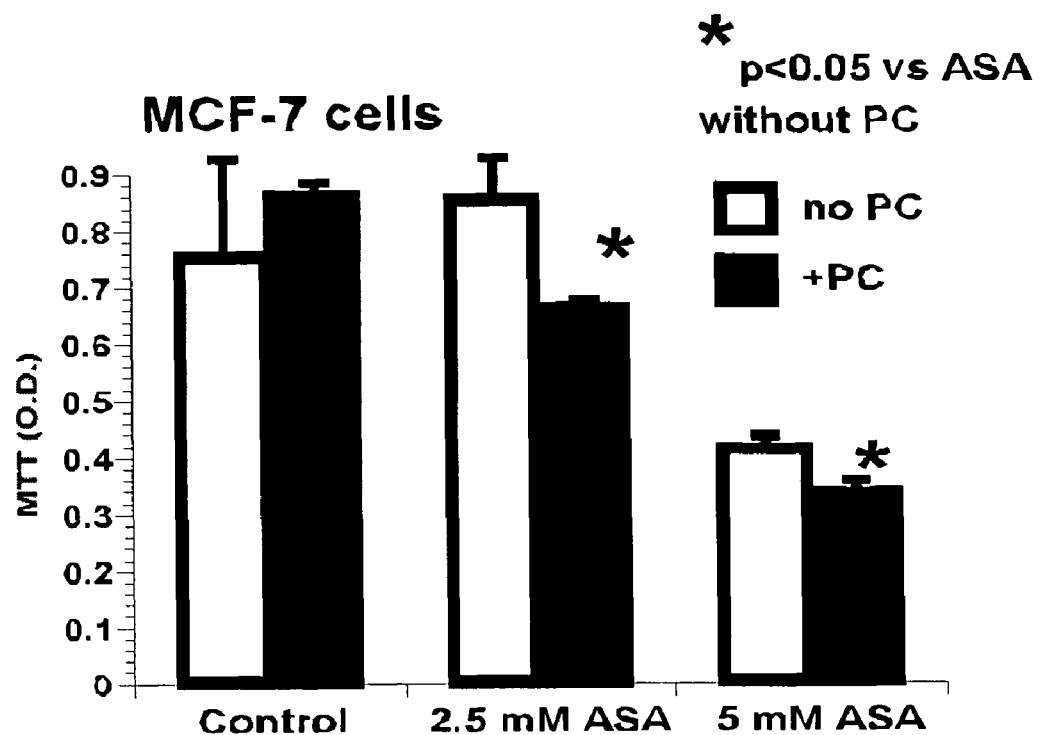
FIG. 3 depicts effect of ASA and Phospholipid-ASA preparation on growth of MCF-7 cells.

To test the relative growth inhibitor activity of phospholipid associated aspirin (PC-ASA) preparations, PC-ASA preparations were made having ASA concentrations that gave no more than 50% inhibition of growth (e.g., 2.5 and 5 mM) as shown in FIG. 2. In this example and in all subsequent examples, cell growth was assessed by measuring mitochondrial 3-(4,5-dimethylthiazol-2-yl)-2,5-diphenyltetrazolium bromide (MTT) activity. Those concentration of ASA were chosen so that any PC effects could be readily observed. After the preparation of the PC-ASA preparation, MCF-7 breast cancer cells were exposed for 48 hours to either ASA or a PC-ASA having the same ASA concentration. Referring now to FIG. 3, the PC-ASA preparations were significantly more effective in inhibiting the growth of the breast cancer cells than the ASA only preparations. It should also be noted that at these relatively low concentrations, PC alone did not adversely affect the growth of the cells (compare open and cross-hatched bars of control cells). These findings demonstrate that in vitro PC-ASA is more efficaceous than unmodified ASA in inhibiting the growth, and even promoting cell death of breast cancer cells.

Figure 4:
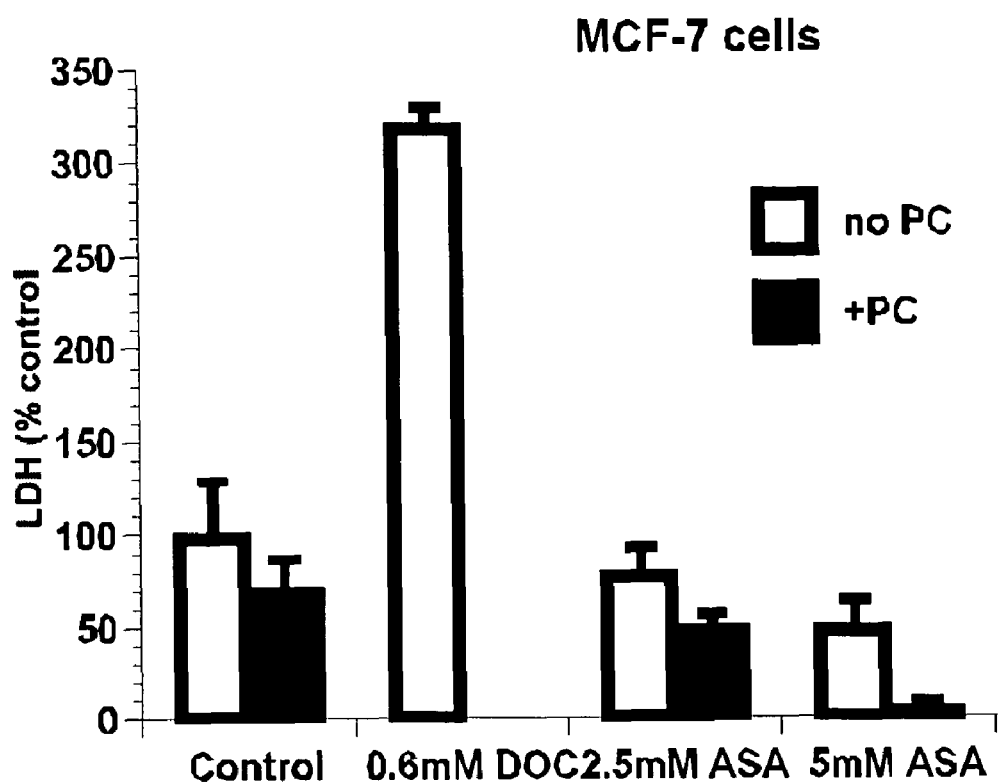
FIG. 4 depicts effect of ASA and Phospholipid-ASA preparation on lactate dehydrogenase (LDH) release (cytolysis-necrosis) of MCF-7 cells.

The growth inhibitor activity of the PC-ASA preparations on MCF-7 cells could be through increased apoptosis or necrosis or inhibition of cell proliferation. To differentiate between the first two possibilities, the effect of the PC-ASA preparations on release of the cytosolic enzyme lactate dehydrogenase (LDH) as a measure of necrosis were performed. For this study, MCF-7 cells were exposed to 2.5 and 5 mM ASA or PC-ASA preparations for 48 hours, as before. The media was collected and assayed for LDH activity (the assay is a kit available from Sigma Chemical Co., St. Louis, Mo.). To act as a positive control, some cells were exposed to a bile acid, 0.6 mM sodium deoxycholate (DOC), for 5 hours before LDH assay. The inventors have found that this concentration of DOC for this time period of exposure to be toxic to cells in culture. As can be seen in FIG. 4, the DOC caused the release of cellular LDH, whereas the NSAIDs did not. Neither the ASA alone, nor the PC-ASA preparation treatments resulted in any suggestion of necrosis of these cells. Yet the ASA and PC-ASA preparations clearly reduce the number of MCF-7 cells at these concentrations. The most likely explanation for these findings is that the NSAIDs are inducing apoptosis rather than necrosis. This possibility is consistent with reports in the literature (see, e.g., Xiaojun L, Xie W, Reed D, Bradshaw W S, Simmons D L. Nonsteroidal antiinflammatory drugs cause apoptosis and induce cyclooxygenases in chicken embryo fibroblasts. *Proc Natl Acad Sci USA* 1995; 92:7961-7965.). Another possibility is that the PC-NSAID act by inhibiting cell proliferation.

Figure 5:
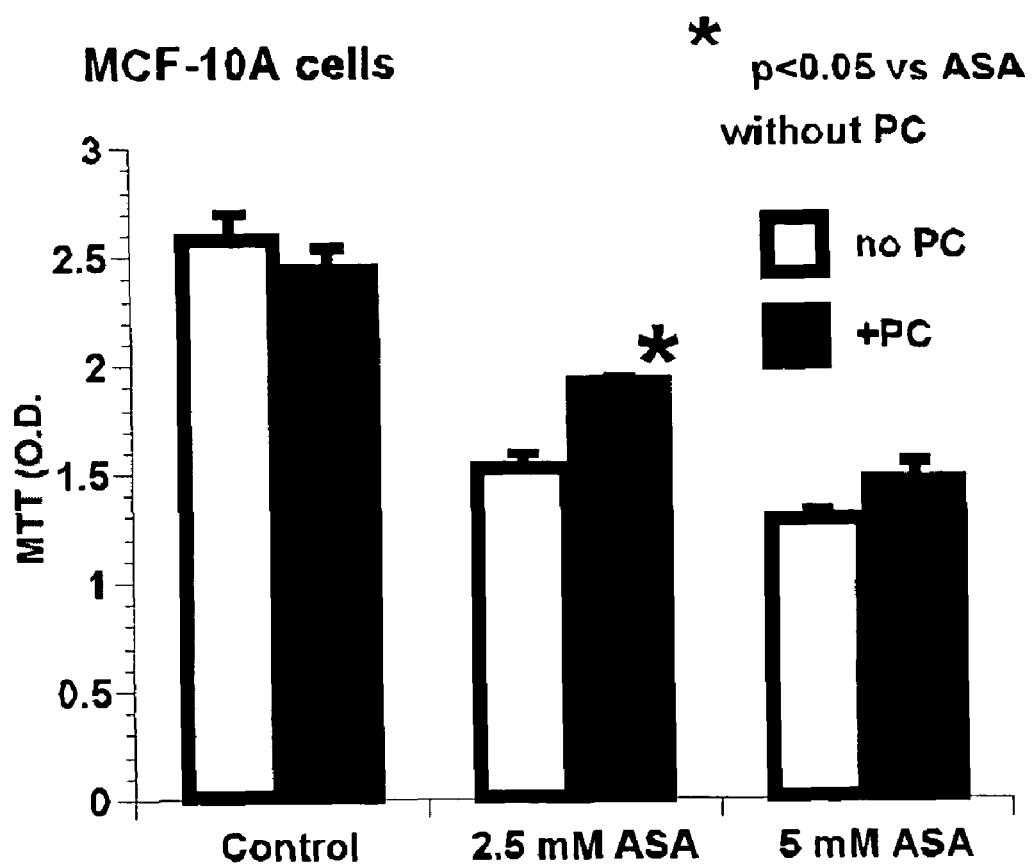
FIG. 5 depicts effect of ASA and Phospholipid-ASA preparation on the growth of normal breast cells.

The effect of ASA and a PC-ASA preparations on a normal breast cell line, MCF-10A, were also investigated. As show in FIG. 5, the PC-ASA preparations had significantly less growth inhibitor activity on this non-cancer cell line than the unmodified ASA. This finding along with our other data suggests that the phospholipid-NSAID preparations may have different effects on cancerous and normal cells, being more affective at inhibiting the growth of cancer cells and less so to normal cells than unmodified NSAIDs, and thus offer an additional benefit over unmodified NSAIDs by preserving normal tissue.

MCF-7 breast cancer cells were grown in culture and exposed to aspirin (acetyl salicylic acid, ASA) and PC-ASA at equimolar concentrations. An assay was performed to estimate cell number. Table 1 shows that PC-ASA was significantly more effective at inhibiting the growth of the breast cancer cells than ASA alone.

TABLE 1

Effect of Aspirin (ASA) and Phosphatidylcholine-Associated Aspirin (PC-ASA) On MCF-7 Breast Cancer Cell Number and DNA Synthesis

| Cell Treatment | Cell Number (% Control) | DNA Synthesis (% Control) |
| --- | --- | --- |
| Control | 100 ± 22 | 100 ± 4 |
| 5 mM ASA | 55 ± 3 | 85 ± 8 |
| 5 mM PC-ASA | 45 ± 3*# | 9 ± 0.2*# |
| 5 mM PC | 114 ± 3 | 41 ± 1*# |

Values expressed as the mean plus-or-minus the standard error of the mean.
*p < 0.05 versus Control
p < 0.05 versus ASA alone It should also be noted that PC alone (at this dose) was not effective at inhibiting the growth of the cells. This in vitro finding demonstrates that the PC-NSAID preparations were more efficaceous than unmodified NSAID preparations at inhibiting the growth, and even promoting cell death of breast cancer cells. Studies were further performed to determine the mechanism by which ASA and PC-ASA reduced cell number. MCF-7 cells were again grown in the absence or presence of ASA and PC-ASA, and cell proliferation was assessed by measurement of titriated thymidine incorporation into cellular DNA. Table 1 shows that the PC-ASA complex was considerably more potent than ASA alone at reducing cell growth as measured by titriated thymidine incorporation.

PC-NSAIDs were also tested on another type of cancer, a colon cancer cell line, SW-480. If was found that PC-ASA and PC-ibuprofen (PC-IBU) were much more effective at reducing SW-480 cell numbers than were the ASA or IBU alone, as seen in Table 2.

TABLE 2

Effect of NSAIDs and PC-NSAIDs on
SW-480 Colon Cancer Cell Number and DNA Synthesis

| Cell treatment | Cell number (% control) | DNA synthesis (% control) |
|---|---|---|
| Control | 100 ± 4 | 100 ± 2 |
| 5 mM ASA | 68 ± 3* | 102 ± 4 |
| 5 mM PC-ASA | 58 ± 1*# | 50 ± 1*# |
| 5 mM PC | 106 ± 7 | 65 ± 4* |
| 1 mM IBU | 81 ± 2* | 79 ± 1* |
| 1 mM PC-IBU | 66 ± 5* | 53 ± 4*# |
| 1 mM PC | 106 ± 13 | 97 ± 5 |

Values are expressed as the mean plus-or-minus the standard error of the mean.
ASA = aspirin;
IBU = ibuprofen;
PC = phosphatidylcholine.
*$p < 0.05$ versus Control
$p < 0.05$ versus ASA or IBU alone Also, the PC-NSAIDs decreased cell proliferation in SW-480 cells to a greater extent than did the ASA or IBU alone, as seen in Table 2. Thus, in two different cancer cell lines, the PC-NSAIDs were more effective in inhibiting the growth of the cancer cells than the NSAIDs alone, and the PC-NSAIDs appeared to act by inhibiting proliferation of the cancer cells.

To confirm that the PC-NSAIDs also have anti-cancer activity in vivo, a study has been performed on a domestic cat. As summarized in Table 3, the animal was diagnosed in December of 2003 with Leiomyosarcoma of the bladder, a particularly aggressive form of cancer.

TABLE 3

Summary of Bladder Cancer in a Cat and PC-Piroxicam
Treatment of the Cancer

| Date | Ultrasonographic findings | Treatment |
|---|---|---|
| Dec. 11, 2003 | Leiomyosarcoma of urinary bladder | Surgical resection and Vincristine weekly × 3 |
| Dec. 31, 2003 | Growth of bladder tumor (tumor width = 3.5 cm) | Lecithin daily |
| Feb. 17, 2004 | No change from previous (tumor width = 3.0 cm) | Lecithin daily |
| Apr. 06, 2004 | Reduction of tumor size (tumor width = 1.9 cm) | Lecithin daily |
| May 20, 2004 | Growth of bladder tumor (tumor occupies 75% of bladder wall) | PC-piroxicam daily$^\alpha$ |
| Jul. 15, 2004 | Reduction in tumor size (tumor width = 1.0 cm) | PC-piroxicam daily$^\alpha$ |

$^\alpha$Piroxicam treatment initiated on May 20, 2004 at a dose of 0.3 mg/kg every other day.

The cat was treated surgically for resection of the tumor and was then placed on standard Vincristine chemotherapy for three weeks. The Vincristine did not stop the remaining tumor growth, and the cat was then treated orally with soy lecithin (phosphatidylcholine) for several months. The lecithin treatment appeared to initially stop and even reduce the tumor size. Eventually, the tumor began to grow again and a treatment of lecithin combined with an NSAID, piroxicam, was begun. The PC-piroxicam appears to be limiting the tumor growth, as assessed by ultrasound, and the cat remains healthy and has gained weight since the administration of PC-piroxicam. The cat is continuing to be treated with PC-piroxicam as of this filing.

In summary, the inventors have obtained data that phospholipid associated NSAID preparations, in addition to its reduced GI toxicity, has utility at inhibiting the growth and/or inducing cell death of breast cancer and colon cancer cell lines. The PC-NSAID preparations are more efficaceous than unmodified NSAIDs in vitro.

REFERENCES

The following references were cited in the above disclosure:

1. Baron, J A. Epidemiology of non-steroidal anti-inflammatory drugs and cancer. *Prog Exp Tumor Res* 2003; 37:1-24.
2. Harris, R E, Namboodiri K K, Farrar W B. Epidemiological study of nonsteroidal anti-inflammatory drugs and breast cancer. *Oncol Rep* 1995; 2:591-592.
3. Wallace J L. Distribution and expression of cyclooxygenase (COX') isoenzymes, their potential physiological roles and the categorization of anti-inflammatory drugs (NSAIDs). *Am J Med* 1999; 107: 11S-17S.
4. Nolan R D, Danilowicz R M, Eling T E. Role of arachidonic acid metabolism in the mitogenic response of BALB/c 3T3 fibroblasts to epidermal growth factor. *Mol Pharmacol* 1988; 33:650-656.
5. Goin M, Pignataro O, Jimenez de Asua L. Early cell cycle diacyglycerol (DAG) content and protein kinase C (PKC) activity enhancement potentiates prostaglandin F2 alpha (PGF2 alpha) induced mitogenesis in Swiss 3T3 CELLS. *Febs Lett* 1993; 316:68-72.
6. Kirkpatrick K, Ogunkolade W, Bustin S, Jenkins P, Ghilchik M, Mokbel K. The mRNA expression of cyclooxygenase-2 and vascular endothelial growth factor in human breast cancer. *Breast Cancer Res Treat* 2001; 69:373.
7. Baek S J, Kim K-S, Nixon J B, Wilson L C, Eling T E. Cyclooxygenase inhibitors regulate the expression of a TGF-β superfamily member that has proapoptotic and antitumorigenic activities. *Mol Pharmacol* 2001; 59:901-908.
8. Baek S J, Wilson L C, Lee C-H, Eling T E. Dual function of nonsteroidal anti-inflammatory drugs (NSAIDs): Inhibition of cyclooxygenase and induction of NSAID-activated gene. *J. Pharmacol Exp Ther* 2002; 301:1126-1131.
9. Bottone F G, Baek S J, Nixon J B, Eling T E. Diallyl disulfide (DADS) induces the antitumorigenic NSAID-activated gene (NAG-1) by a p53-dependent mechanism in human colorectal HCT 116 cells. *J. Nutr* 2002; 132:773-778.
10. Kim K-S, Baek S J, Flake G P, Loftin C D, Calvo B F, Eling T E. Expression and regulation of nonsteroidal anti-inflammatory drug-activated gene (NAG-1) in human and mouse tissue. *Gastroenterology* 2002; 122:1388-1398.
11. Yamato Y, Yin M J, Lin K M, Gaynor R B. Sulindac inhibits activation of the NFκB pathway. *J. Biol Chem,* 1999; 274:27307-27314.
12. Berman K S, Verma U N, Harburg G, Minna J D, Cobb M H, Gaynor R B. Sulindac enhances tumor necrosis factor-alpha-mediated apoptosis of lung cancer cell lines by inhibition of nuclear factor-kappaB. *Clin Cancer Res* 2002; 8:354-360.
13. Zhang L, Yu J, Park B H, Kinzler K W, Vogelstein B. Role of BAX in the apoptotic response to anticancer agents. *Science* 2000; 290:989-992.

14. Soh J W, Mao Y, Kim M G, Pamukcu R, Li H, Piazza G A, Thonpson W J, Weinstein I B. Cyclic GMP mediates apoptosis induced by sulindac derivatives via activation of c-Jun NH2-terminal kinase 1. *Clin Cancer Res* 2000; 6:4136-4141.
15. Gabriel, S E, Jaakkimainen L, Bombardier C. Risk for serious gastrointestinal complications related to use of nonsteroidal anti-inflammatory drugs. A meta-analysis. *Ann Intern Med,* 1991; 115: 787-96.
16. Wallace J L. Nonsteroidal anti-inflammatory drugs and gastroenteropathy: the second hundred years. *Gastroenterology* 1997; 112: 1000-1016.
17. Weil J, Colin-Jones D, Langman M. Lawson D, Logan R, Murphy M et al. Prophylactic aspirin and risk of peptic ulcer bleeding. *BMJ* 1995; 310:827-830.
18. Cryer B, Feldman M. Effects of very low dose daily aspirin on gastric, duodenal and rectal prostaglandins and mucosal injury. *Gastroenterology* 1999; 117:17-25.
19. Lichtenberger, L M, Wang Z-M, Romero J J, Ulloa C, Perez J C, Giraud M-N, Barreto J C. Non-steroidal anti-inflammatory drugs (NSAIDs) associate with zwitterionic phospholipids: insight into the mechanism and reversal of NSAID-induced gastrointestinal injury. *Nature Med,* 1995; 1: 154-158.
20. Lichtenberger, L M, Romero J J, De Ruijter W M J, Behbod F, Darling R, Ashraf A Q, Sanduja S K. Phosphatidylcholine association increases the anti-inflammatory and analgesic activity of ibuprofen in acute and chronic rodent models of joint inflammation: relationship to alterations in bioavailability and cyclooxygenase-inhibitory potency. *J Pharmacol Exp Therap.* 2001; 298: 279-87.

All references cited are incorporated herein by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which hereafter.

We claim:

1. A method for inhibiting the growth of bladder cancer cells, breast cancer cells, or colon cancer cells comprising the steps of:

administering to the body of an animal or directly into the site of cancerous growth in an animal afflicted with bladder cancer, breast cancer, or colon cancer, or directly into a site of cancerous growth, a composition comprising an associated complex of a phospholipid and a nonsteroidal anti-inflammatory pharmaceutical (NSAID);

wherein said associated complex of said phospholipid and said NSAID inhibits the growth of said bladder cancer cells, said breast cancer cells, or said colon cancer cells more than NSAID alone in inhibiting the growth of said bladder cancer cells, said breast cancer cells, or said colon cancer cells;

wherein said NSAID is aspirin, piroxicam, or ibuprofen; and wherein said phospholipid is dipalmitoyl phosphatidylcholine, phosphatidyl choline, or mixtures thereof.

2. The method of claim 1, wherein the composition is a buffered or hypotonic aqueous composition.

* * * * *